(12) United States Patent
Schultze et al.

(10) Patent No.: US 10,172,780 B2
(45) Date of Patent: Jan. 8, 2019

(54) ACRYLIC POLYMER OF MALEIC ANHYDRIDE AND USE THEREOF IN COSMETICS

(71) Applicant: L'OREAL, Paris (FR)

(72) Inventors: Xavier Schultze, Les Pavillons sous Bois (FR); Franck Hernandez, Villemomble (FR); Bertrand Lion, Paris (FR)

(73) Assignee: L'OREAL, Paris (FR)

( * ) Notice: Subject to any disclaimer, the term of this patent is extended or adjusted under 35 U.S.C. 154(b) by 6 days.

(21) Appl. No.: 15/515,282

(22) PCT Filed: Sep. 29, 2015

(86) PCT No.: PCT/EP2015/072460
§ 371 (c)(1),
(2) Date: Mar. 29, 2017

(87) PCT Pub. No.: WO2016/050785
PCT Pub. Date: Apr. 7, 2016

(65) Prior Publication Data
US 2017/0216185 A1      Aug. 3, 2017

(30) Foreign Application Priority Data

Sep. 30, 2014   (FR) ..................... 14 59232

(51) Int. Cl.

| | | |
|---|---|---|
| *A61K 8/81* | (2006.01) | |
| *A61Q 19/08* | (2006.01) | |
| *C08F 220/18* | (2006.01) | |
| *A61K 8/02* | (2006.01) | |
| *A61K 8/04* | (2006.01) | |
| *A61K 8/19* | (2006.01) | |
| *A61K 8/31* | (2006.01) | |
| *A61K 8/37* | (2006.01) | |
| *A61K 8/58* | (2006.01) | |
| *A61Q 1/02* | (2006.01) | |
| *A61Q 1/04* | (2006.01) | |
| *A61Q 1/06* | (2006.01) | |
| *A61Q 1/10* | (2006.01) | |
| *C08F 220/06* | (2006.01) | |
| *C08F 265/06* | (2006.01) | |
| *C08L 33/08* | (2006.01) | |

(52) U.S. Cl.
CPC .......... *A61K 8/8164* (2013.01); *A61K 8/0216* (2013.01); *A61K 8/04* (2013.01); *A61K 8/19* (2013.01); *A61K 8/31* (2013.01); *A61K 8/37* (2013.01); *A61K 8/58* (2013.01); *A61K 8/8152* (2013.01); *A61Q 1/02* (2013.01); *A61Q 1/04* (2013.01); *A61Q 1/06* (2013.01); *A61Q 1/10* (2013.01); *A61Q 19/08* (2013.01); *C08F 220/06* (2013.01); *C08F 220/18* (2013.01); *C08F 265/06* (2013.01); *C08L 33/08* (2013.01); *A61K 2800/31* (2013.01); *A61K 2800/43* (2013.01); *A61K 2800/594* (2013.01); *C08F 2220/1808* (2013.01); *C08F 2220/1875* (2013.01)

(58) Field of Classification Search
None
See application file for complete search history.

(56) References Cited

U.S. PATENT DOCUMENTS

| | | |
|---|---|---|
| 5,185,143 A | 2/1993 | Cohen |
| 2014/0227210 A1* | 8/2014 | Farcet ................. A61K 8/8152 424/59 |

FOREIGN PATENT DOCUMENTS

| | | |
|---|---|---|
| FR | 2972630 A1 | 9/2012 |
| JP | P2011 046868 A | 3/2011 |

OTHER PUBLICATIONS

International Search Report and Written Opinion dated Jan. 11, 2013 issued in International Application No. PCT/EP2012/063615.

\* cited by examiner

*Primary Examiner* — Brian Gulledge
(74) *Attorney, Agent, or Firm* — Polsinelli PC

(57) ABSTRACT

The invention relates to a copolymer resulting from the polymerization of:
  (a) 50% to 90% by weight, of the total weight of monomers, of isobornyl (meth)acrylate,
  (b) 1% to 50% by weight of maleic anhydride,
  (c) 0% to 49% by weight of additional (meth)acrylate monomer chosen from:
    (i) saturated or unsaturated and linear or branched $C_1$-$C_{20}$ alkyl (meth)acrylates, the alkyl being optionally interrupted by one or more nonadjacent heteroatoms chosen from O or S or by an NR group, R being a $C_1$-$C_4$ alkyl group, optionally substituted by a phenyl or furfuryl group;
    (ii) saturated $C_4$-$C_8$ cycloalkyl (meth)acrylates, the cycloalkyl being optionally interrupted by O or NH.
The invention also relates to a composition comprising said copolymer in a physiologically acceptable medium.
The invention also relates to a cosmetic method for caring for or making up the skin or the lips, comprising the topical application, to the skin or the lips, of a cosmetic composition comprising said copolymer.

20 Claims, No Drawings

ACRYLIC POLYMER OF MALEIC ANHYDRIDE AND USE THEREOF IN COSMETICS

CROSS REFERENCE TO RELATED APPLICATIONS

This application is a National Phase filing under 35 U.S.C. § 371 of PCT/EP2015/072460 filed on Sep. 29, 2015; and this application claims priority to Application No. 1459232 filed in France on Sep. 30, 2014 under 35 U.S.C. § 119. The entire contents of each application are hereby incorporated by reference.

The present invention relates to a maleic anhydride acrylic polymer, to a composition comprising such a polymer and to the use of this polymer in the cosmetics field.

During the aging process, various signs appear on the skin which are very characteristic of this aging, being reflected in particular by a modification of skin structure and functions. The main clinical signs of skin aging are in particular the appearance of deep wrinkles and fine lines, which increase with age.

It is known to treat these signs of aging using cosmetic or dermatological compositions containing active agents capable of combating aging, such as α-hydroxy acids, β-hydroxy acids and retinoids. These active agents act on wrinkles by eliminating dead skin cells and by accelerating the cell renewal process. However, these active agents exhibit the disadvantage of being effective for the treatment of wrinkles only after a certain application time. In point of fact, it is increasingly sought to obtain an immediate effect of the active agents used, rapidly resulting in smoothing-out of wrinkles and fine lines and in the disappearance of the signs of fatigue.

The inventors have discovered that a specific maleic anhydride acrylic polymer as described below exhibits good film-forming properties. When the polymer is applied to the skin, it has a good tightening effect on the skin and thus makes it possible to attenuate skin wrinkles immediately. This tightening effect also exhibits good water resistance. This specific acrylic polymer is readily conveyable in a hydrocarbon oil, such as isododecane. This polymer is thus highly suitable for preparing anhydrous compositions with a tightening effect having a good water resistance. In addition, the film obtained with the polymer exhibits a good water resistance.

These film-forming polymers are also suitable for making up the skin or the lips, such as foundations or lipsticks.

More specifically, a subject matter of the present invention is a copolymer resulting from the polymerization of:
 (a) 50% to 90% by weight, of the total weight of monomers, of isobornyl (meth)acrylate,
 (b) 1% to 50% by weight of maleic anhydride,
 (c) 0% to 49% by weight of additional (meth)acrylate monomer chosen from:
  (i) saturated or unsaturated and linear or branched $C_1$-$C_{20}$ alkyl (meth)acrylates, the alkyl being optionally interrupted by one or more nonadjacent heteroatoms chosen from O or S or by an NR group, R being a $C_1$-$C_4$ alkyl group, optionally substituted by a phenyl or furfuryl group;
  (ii) saturated $C_4$-$C_8$ cycloalkyl (meth)acrylates, the cycloalkyl being optionally interrupted by O or NH.

Such a copolymer is referred to subsequently as acrylic polymer.

Another subject matter of the invention is a composition comprising, in a physiologically acceptable medium, an acrylic polymer as described above.

Another subject matter of the invention is a method, in particular a cosmetic method, for caring for or making up the skin or the lips, more particularly the skin of the face, in particular wrinkled skin, comprising the topical application to the skin or lips of a composition, in particular a cosmetic composition, comprising an acrylic polymer as described above.

Another subject matter of the invention is a method, in particular a cosmetic method, for caring for the skin, more particularly for the skin of the face, in particular for wrinkled skin, comprising the topical application to the skin of a composition, in particular a cosmetic composition, comprising an acrylic polymer as described above.

The method according to the invention is in particular intended to smooth out human facial and/or body skin and/or to decrease or efface the signs of skin aging, in particular to reduce or efface wrinkles and/or fine lines of the skin.

Another subject matter of the invention is the cosmetic use as tightening agent for the skin, in particular for wrinkled skin, of an acrylic polymer as described above or of a composition containing it and comprising a physiologically acceptable medium, as defined below.

"Tightening agent" is intended to mean compounds capable of having a noticeable tightening effect, that is to say of smoothing out the skin and immediately reducing the wrinkles and fine lines, indeed even making them disappear.

The tightening effect can be characterized by an in vitro retraction test as described in example 4.

The acrylic polymer according to the invention comprises an isobornyl (meth)acrylate, maleic anhydride and optionally an additional (meth)acrylate monomer as defined above. Advantageously, the acrylic polymer is composed essentially of these monomers according to the contents described above.

Advantageously, the polymer according to the invention results from the polymerization of:
 (a) 50% to 90% by weight, of the total weight of monomers, of isobornyl (meth)acrylate,
 (b) 5% to 50% by weight of maleic anhydride,
 (c) 0% to 30% by weight of additional (meth)acrylate monomer as described above.

Advantageously, the polymer according to the invention results from the polymerization of:
 (a) 50% to 80% by weight, of the total weight of monomers, of isobornyl (meth)acrylate,
 (b) 5% to 30% by weight of maleic anhydride,
 (c) 15 to 30% by weight of additional (meth)acrylate monomer as described above.

Advantageously, the polymer according to the invention results from the polymerization of:
 (a) 50% to 80% by weight, of the total weight of monomers, of isobornyl (meth)acrylate,
 (b) 5% to 25% by weight of maleic anhydride,
 (c) 15 to 30% by weight of additional (meth)acrylate monomer as described above.

Advantageously, the polymer according to the invention results from the polymerization of:
 (a) 50% to 80% by weight, of the total weight of monomers, of isobornyl (meth)acrylate,
 (b) 5% to 15% by weight of maleic anhydride,
 (c) 15 to 30% by weight of additional (meth)acrylate monomer as described above.

Advantageously, the polymer according to the invention results from the polymerization of:
 (a) 60% to 80% by weight, of the total weight of monomers, of isobornyl (meth)acrylate,
 (b) 5% to 12% by weight of maleic anhydride, (c) 15 to 30% by weight of additional (meth)acrylate monomer as described above.

Advantageously, the polymer according to the invention results from the polymerization of:
(a) 60% to 80% by weight, of the total weight of monomers, of isobornyl (meth)acrylate,
(b) 5% to 12% by weight of maleic anhydride,
(c) 18 to 30% by weight of additional (meth)acrylate monomer as described above.

The additional (meth)acrylate monomer is preferably chosen from $C_6$-$C_{16}$ alkyl (meth)acrylates and preferentially chosen from $C_6$-$C_{16}$ alkyl acrylates. Mention may be made, as examples of $C_6$-$C_{16}$ alkyl (meth)acrylate, of hexyl (meth)acrylate, octyl (meth)acrylate, 2-ethylhexyl (meth)acrylate, decyl (meth)acrylate and lauryl (meth)acrylate. 2-Ethylhexyl acrylate is preferably used.

Preferably, the polymer according to the invention comprises, or consists of, isobornyl acrylate, 2-ethylhexyl acrylate and maleic anhydride.

A polymer which is particularly preferred is the polymer resulting from the polymerization of:
(a) 50% to 80% by weight, of the total weight of monomers, of isobornyl (meth)acrylate,
(b) 5% to 30% by weight of maleic anhydride,
(c) 15% to 30% by weight of $C_6$-$C_{16}$ alkyl acrylate monomer.

A polymer which is particularly preferred is the polymer resulting from the polymerization of:
(a) 50% to 80% by weight, of the total weight of monomers, of isobornyl (meth)acrylate,
(b) 5% to 25% by weight of maleic anhydride,
(c) 15% to 30% by weight of $C_6$-$C_{16}$ alkyl acrylate monomer.

A polymer which is particularly preferred is the polymer resulting from the polymerization of:
(a) 50% to 80% by weight, of the total weight of monomers, of isobornyl (meth)acrylate,
(b) 5% to 15% by weight of maleic anhydride,
(c) 15% to 30% by weight of $C_6$-$C_{16}$ alkyl acrylate monomer.

A polymer which is particularly preferred is the polymer resulting from the polymerization of:
(a) 60% to 80% by weight, of the total weight of monomers, of isobornyl (meth)acrylate,
(b) 5% to 12% by weight of maleic anhydride,
(c) 15% to 30% by weight of $C_6$-$C_{16}$ alkyl acrylate monomer.

A polymer which is particularly preferred is the polymer resulting from the polymerization of:
(a) 60% to 80% by weight, of the total weight of monomers, of isobornyl (meth)acrylate,
(b) 5% to 12% by weight of maleic anhydride,
(c) 18% to 30% by weight of $C_6$-$C_{16}$ alkyl acrylate monomer.

Advantageously, the polymer according to the invention consists of the monomers described above.

Advantageously, the polymer according to the invention is nonionic.

Preferably, the acrylic polymer according to the invention has a weight-average molecular weight ranging from 5000 to 1 000 000 g/mol, preferably ranging from 10 000 to 500 000 g/mol and preferentially ranging from 15 000 to 350 000 g/mol.

The molecular weight can in particular be determined by size exclusion chromatography, THF eluent, polystyrene standard, 2414 refractometric detector from Waters.

The copolymer can be a random, alternating (block) or gradient polymer. Preferably, the copolymer is random.

The copolymer according to the invention can be prepared by radical polymerization of the monomers described above, in particular as a mixture or sequentially added during the polymerization, in particular by using an organic solvent having a boiling point of greater than or equal to 60° C., such as, for example, isododecane, ethanol, ethyl acetate, tetrahydrofuran, methyltetrahydrofuran or methyl ethyl ketone. The organic solvent makes it possible to dissolve the monomers used and the polymer formed.

The polymerization is in particular carried out in the presence of a radical initiator, in particular of peroxide type (for example, tert-butyl peroxy-2-ethylhexanoate: Trigonox 21S; 2,5-dimethyl-2,5-di(2-ethylhexanoylperoxy)hexane: Trigonox 141; tert-butyl peroxypivalate: Trigonox 25C75 from AkzoNobel) or of azo type (for example, AIBN: azobisisobutyronitrile; V50: 2,2'-azobis(2-amidinopropane) dihydrochloride).

The polymerization can be carried out at a temperature ranging from 60 to 100° C. and preferably ranging from 60 to 85° C.

The duration of the polymerization can be approximately 24 hours.

The polymer according to the invention can be used in a composition comprising a physiologically acceptable medium, in particular in a cosmetic composition.

Physiologically acceptable medium is understood to mean a medium compatible with human keratinous substances, in particular with the skin.

Cosmetic composition is understood to mean a composition which is compatible with keratinous substances, which exhibits a pleasant color, odor and feel and which does not cause unacceptable discomfort (stinging, tautness or redness) liable to turn the consumer away from it.

The acrylic polymer as defined above can be present in the composition according to the invention in a content ranging from 0.1% to 10% by weight, with respect to the total weight of the composition, preferably from 0.5% to 10% by weight of active material, preferentially ranging from 1% to 8% by weight and more preferentially ranging from 1% to 6% by weight.

The composition used according to the invention is generally suitable for topical application to the skin or the lips and thus generally comprises a physiologically acceptable medium, that is to say a medium compatible with the skin and/or its superficial body growths. It is preferably a cosmetically acceptable medium, that is to say a medium which exhibits a pleasant color, odor and feel and which does not cause unacceptable discomfort (stinging, tautness or redness) liable to discourage the consumer from using this composition.

According to a preferred embodiment of the invention, the composition comprising the polymer can contain a hydrocarbon oil.

The hydrocarbon oil is an oil which is liquid at ambient temperature (25° C.).

Hydrocarbon oil is understood to mean an oil formed essentially from, indeed even consisting of, carbon and hydrogen atoms and optionally oxygen and nitrogen atoms, and not containing a silicon or fluorine atom. It can contain alcohol, ester, ether, carboxylic acid, amine and/or amide groups.

The hydrocarbon oil can be volatile or nonvolatile.

The hydrocarbon oil can be chosen from:
hydrocarbon oils having from 8 to 14 carbon atoms and in particular:

branched $C_8$-$C_{14}$ alkanes, such as $C_8$-$C_{14}$ isoalkanes of petroleum origin (also known as isoparaffins), such as isododecane (also known as 2,2,4,4,6-pentamethylheptane), isodecane and, for example, the oils sold under the Isopar or Permethyl trade names, linear alkanes, for example such as n-dodecane ($C_{12}$) and n-tetradecane ($C_{14}$) sold by Sasol respectively under the references Parafol 12-97 and Parafol 14-97, and also their mixtures, the undecane-tridecane mixture, the mixtures of n-undecane ($C_{11}$) and of n-tridecane ($C_{13}$) obtained in examples 1 and 2 of the patent application WO 2008/155059 from Cognis, and their mixtures, short-chain esters (having from 3 to 8 carbon atoms in total), such as ethyl acetate, methyl acetate, propyl acetate or n-butyl acetate, hydrocarbon oils of vegetable origin, such as triglycerides consisting of esters of fatty acids and of glycerol, the fatty acids of which can have varied chain lengths from $C_4$ to $C_{24}$, it being possible for these chains to be saturated or unsaturated and linear or branched; these oils are in particular heptanoic acid or octanoic acid triglycerides, or alternatively wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkinseed oil, cucumber oil, blackcurrant oil, evening primrose oil, millet oil, barley oil, quinoa oil, rye oil, safflower oil, candlenut oil, passionflower oil or musk rose oil; shea butter; or also triglycerides of caprylic/capric acids, such as those sold by Stéarineries Dubois or those sold under the names Miglyol 810®, 812® and 818® by Dynamit Nobel, synthetic ethers having from 10 to 40 carbon atoms;

linear or branched hydrocarbons of mineral or synthetic origin, such as liquid petrolatum, polydecenes, hydrogenated polyisobutene, such as Parleam®, squalane or liquid paraffins, and their mixtures, synthetic esters, such as oils of formula $R_1COOR_2$ in which $R_1$ represents the residue of a linear or branched fatty acid comprising from 1 to 40 carbon atoms and $R_2$ represents an in particular branched hydrocarbon chain containing from 1 to 40 carbon atoms, provided that $R_1+R_2 \geq 10$, for example purcellin oil (cetearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, heptanoates, octanoates, decanoates or ricinoleates of alcohols or of polyalcohols, such as propylene glycol dioctanoate; hydroxylated esters, such as isostearyl lactate, diisostearyl malate or 2-octyldodecyl lactate; polyol esters and pentaerythritol esters, fatty alcohols which are liquid at ambient temperature comprising a branched and/or unsaturated carbon chain having from 12 to 26 carbon atoms, such as octyldodecanol, isostearyl alcohol, oleyl alcohol, 2-hexyldecanol, 2-butyloctanol and 2-undecylpentadecanol.

Advantageously, the hydrocarbon oil is nonpolar (thus formed solely of carbon and hydrogen atoms).

The hydrocarbon oil is preferably chosen from hydrocarbon oils having from 8 to 14 carbon atoms, in particular the nonpolar oils described above.

Preferably, the hydrocarbon oil is isododecane.

The composition comprising the polymer can contain, in addition to the hydrocarbon oil, a silicone oil. "Silicone oil" is understood to mean an oil comprising at least one silicon atom and in particular at least one Si—O group. The silicone oil may be volatile or nonvolatile.

"Volatile oil" is understood to mean an oil (or nonaqueous medium) capable of evaporating on contact with the skin in less than one hour, at ambient temperature and at atmospheric pressure. The volatile oil is a volatile cosmetic oil, which is liquid at ambient temperature, which has in particular a nonzero vapor pressure, at ambient temperature and at atmospheric pressure, in particular which has a vapor pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

"Nonvolatile oil" is understood to mean an oil having a vapor pressure of less than 0.13 Pa.

Mention may be made, as volatile silicone oils, of volatile linear or cyclic silicone oils, in particular those having a viscosity $\leq 8$ centistokes (cSt) ($8 \times 10^{-6}$ m$^2$/s) and having in particular from 2 to 10 silicon atoms and especially from 2 to 7 silicon atoms, these silicones optionally comprising alkyl or alkoxy groups having from 1 to 10 carbon atoms. Mention may in particular be made, as volatile silicone oil which can be used in the invention, of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and their mixtures.

Mention may be made, as nonvolatile silicone oils, of nonvolatile linear or cyclic polydimethylsiloxanes (PDMSs); polydimethylsiloxanes comprising alkyl, alkoxy or phenyl groups, which groups are pendent or at the end of the silicone chain and have from 2 to 24 carbon atoms; phenylated silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Advantageously, the composition can comprise a hydrocarbon oil in a content ranging from 60% to 100% by weight of the total weight of the oils present in the composition and from 0 to 40% by weight of silicone oil. According to a preferred embodiment of the invention, the composition contains, as oil, only a hydrocarbon oil.

The composition according to the invention can comprise a cosmetic additive chosen from water, fragrances, preservatives, fillers, UV-screening agents, oils, waxes, surfactants, moisturizing agents, vitamins, ceramides, antioxidants, agents for combating free radicals, polymers, thickeners and colorants.

The composition according to the invention can also comprise a colorant, such as pulverulent colorants, fat-soluble dyes or water-soluble dyes. This colorant can be present in a content ranging from 0.01% to 30% by weight, with respect to the total weight of the composition.

The pulverulent colorants can be chosen from pigments and pearlescent agents.

The pigments can be white or colored, inorganic and/or organic and coated or uncoated. Mention may be made, among inorganic pigments, of titanium dioxide, optionally surface-treated, zirconium, zinc or cerium oxides, and also iron or chromium oxides, manganese violet, ultramarine blue, chromium hydrate and ferric blue. Mention may be made, among organic pigments, of carbon black, pigments of D & C type and lakes based on cochineal carmine of barium, strontium, calcium or aluminum.

The pearlescent agents can be chosen from white pearlescent pigments, such as mica covered with titanium or with bismuth oxychloride, colored pearlescent pigments, such as titanium oxide-coated mica with iron oxides, titanium oxide-coated mica with in particular ferric blue or chromium oxide or titanium oxide-coated mica with an organic pigment of the abovementioned type, and also pearlescent pigments based on bismuth oxychloride.

The fat-soluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

Of course, a person skilled in the art will take care to choose this or these optional additional compounds and/or their amounts such that the antiwrinkle properties of the composition according to the invention are not, or not substantially, detrimentally affected by the envisaged addition.

Advantageously, the composition according to the invention is a skin care composition.

The composition according to the invention can be a makeup composition, such as a foundation, a lipstick or an eye liner.

According to one embodiment, the composition according to the invention is a makeup composition and comprises a volatile oil and a nonvolatile oil as are described above. In particular, the makeup composition can comprise a volatile hydrocarbon oil and a nonvolatile hydrocarbon oil.

According to one embodiment, the composition according to the invention is an anhydrous composition. "Anhydrous composition" is understood to mean a composition containing less than 2% by weight of water, indeed even less than 0.5% of water, and in particular devoid of water. If appropriate, such small amounts of water may in particular be introduced by ingredients of the composition which may contain residual amounts thereof. The application of the cosmetic composition used according to the invention is carried out according to the usual techniques, for example by application (in particular of creams, gels, serums or lotions) to the skin intended to be treated, in particular the skin of the face and/or neck, especially the skin of the outline of the eye. In the context of this method, the composition can, for example, be a care composition.

The invention is illustrated in greater detail in the following examples.

EXAMPLE 1: ISOBORNYL ACRYLATE/2-ETHYLHEXYL ACRYLATE/MALEIC ANHYDRIDE COPOLYMER (70/20/10 BY WEIGHT)

70 g of isobornyl acrylate, 20 g of 2-ethylhexyl acrylate and 10 g of maleic anhydride were introduced into a jacketed 1-liter reactor equipped with an anchor stirrer. A mixture of 70 g of isododecane and 30 g of ethyl acetate was subsequently added. The medium was brought to a temperature of 40° C. with stirring (150 revolutions/min) and bubbling with argon was carried out for 10 minutes, followed by addition of 0.5 g of initiator tert-butyl peroxy-2-ethylhexanoate Trigonox 21S (Trigonox® 21S from AkzoNobel).

The heating of the jacket was adjusted to 90° C. for 7 hours at 150 revolutions/min.

The medium was subsequently diluted with 300 g of isododecane and then concentrated by distillation in order to remove the ethyl acetate and the unreacted maleic anhydride. A 30% by weight solution of the copolymer in isododecane (yield greater than 90%) was finally obtained.

The polymer obtained has a molecular weight (Mw) of close to 200 000 g/mol.

EXAMPLE 2: ISOBORNYL ACRYLATE/2-ETHYLHEXYL ACRYLATE/MALEIC ANHYDRIDE COPOLYMER (65/25/10 BY WEIGHT)

The polymer was prepared according to the procedure of example 1, using 65 g of isobornyl acrylate, 25 g of 2-ethylhexyl acrylate and 10 g of maleic anhydride.

A 30% by weight solution of the copolymer in isododecane (yield greater than 90%) was finally obtained.

The polymer obtained has a molecular weight (Mw) of close to 200 000 g/mol.

EXAMPLE 3: ISOBORNYL ACRYLATE/2-ETHYLHEXYL ACRYLATE/MALEIC ANHYDRIDE COPOLYMER (75/20/5 BY WEIGHT)

The polymer was prepared according to the procedure of example 1, using 75 g of isobornyl acrylate, 20 g of 2-ethylhexyl acrylate and 10 g of maleic anhydride.

A 30% by weight solution of the copolymer in isododecane (yield greater than 90%) was finally obtained.

The polymer obtained has a molecular weight (Mw) of close to 200 000 g/mol.

EXAMPLE 4: ISOBORNYL ACRYLATE/2-ETHYLHEXYL ACRYLATE/MALEIC ANHYDRIDE COPOLYMER (60/20/20 BY WEIGHT)

The polymer was prepared according to the procedure of example 1, using 60 g of isobornyl acrylate, 20 g of 2-ethylhexyl acrylate and 20 g of maleic anhydride.

A 36% by weight solution of the copolymer in isododecane (yield greater than 90%) was finally obtained.

The polymer obtained has a molecular weight (Mw) of close to 200 000 g/mol.

EXAMPLE 5

Demonstration of the Tightening Effect of the Polymers Used According to the Invention This test consists in comparing, in vitro, the tightening power of the polymer to be evaluated, with respect to a reference tightening polymer: Hybridur® 875 polymer dispersion from Air Products (40% by weight aqueous dispersion of particles of an interpenetrated network of polyurethane and acrylic polymers). The polymer to be evaluated was deposited on a nitrile rubber strip cut from a glove sold under the reference Safeskin Nitrile Criticial No. 038846 by Dominique Dutscher SA, with a surface area of 3.5 cm², stretched taut beforehand on a support. An aqueous solution containing the polymer to be evaluated is thus deposited on the elastomer strip, by depositing 1.8 mg (as dry matter) of polymer.

26 μl of an aqueous solution containing 7% AM of Hybridur® 875 polymer were thus deposited on a nitrile rubber strip in order to thus obtain a reference tightening strip, and 26 μl of a solution containing 7% AM of acrylic polymer to be evaluated in an isododecane/ethanol mixture (70/30 weight/weight) were deposited on another strip. After drying at room temperature (25° C.) for 24 hours, the curving (retraction) of the strip treated with the acrylic polymer is observed in comparison with that obtained with the control (Hybridur® 875).

The tightening effect, obtained according to the protocol described above, of the polymers of examples 1 to 3 was measured. The resistance to water of the tightening effect was then also evaluated by immersing the rubber strips treated with the polymer to be evaluated in water at ambient temperature (25° C.) for 10 minutes, followed by evaluating the tightening effect after drying for 1 hour.

The following results were obtained:

| Polymer tested | Tightening effect | Tightening effect after immersion in water |
|---|---|---|
| Hybridure 875 reference | correct | correct |
| Example 1 | greater than the reference | greater than the reference |
| Example 2 | comparable to the reference | greater than the reference |
| Example 3 | comparable to the reference | greater than the reference |

The results obtained show that the polymers of examples 1 to 3 form a film which exhibits a good tightening effect, including after immersion in water.

EXAMPLE 6

An antiwrinkle gel having the following composition is prepared:

| | |
|---|---|
| polymer of example 1 as a 30% by weight solution in isododecane | 7 g AM |
| disteardimonium hectorite/ propylene carbonate in isododecane (bentone gel ® ISDV from Elementis) | 3 g |
| Preservatives | q.s. |
| Isododecane/ethanol (80/20 w/w) | q.s. for 100 g |

A similar composition is also prepared using the polymer of example 2 or 3 or 4.

The composition obtained, applied to the face, makes it possible to effectively smooth out wrinkles.

EXAMPLES 7 to 14: COSMETIC EVALUATION OF MAKEUP COMPOSITIONS

The 8 makeup compositions according to the invention which are described below were prepared.

Each composition was applied on a skin equivalent support made of elastomer by producing a deposited layer with a wet thickness of 100 µm, which was left to dry at ambient temperature (25° C.) for 24 hours.

The state of the film obtained was subsequently observed.

The resistance to water of the film obtained was evaluated by applying 0.5 ml of water; after 5 minutes of contact, the surface of the film was rubbed with a cotton swab and then the state of the film was observed.

The tackiness of the film and its ability to transfer or not transfer on touching the film with a finger were also evaluated.

The evaluation was carried out in the following way:
+++: cosmetic property evaluated as very effective
++: cosmetic property evaluated as moderately effective
+: cosmetic property evaluated as not very effective
0: cosmetic property evaluated as not effective The following results were obtained:

| | Example 7 | Example 8 | Example 9 | Example 10 |
|---|---|---|---|---|
| Polymer of example 1 | 20 g | 20 g | 20 g | 20 g |
| Pigment paste comprising 40% by weight of pigment in isododecane | 5 g with DC Red 7 | 5 g with DC Red 7 | 5 g with black iron oxide | 5 g with black iron oxide |
| Disteardimonium hectorite (Bentone Gel ISD V from Elementis) | 10 g | 10 g | 10 g | 10 g |
| Isododecane | 65 g | 45 g | 65 g | 45 g |
| 2-Octyldodecanol | — | 20 g | — | 20 g |
| Appearance of the film | Homogeneous film | Homogeneous film | Homogeneous film | Homogeneous film |
| Resistance to water | +++ | +++ | +++ | +++ |
| Non-tacky | +++ | +++ | +++ | +++ |
| Transfer-resistant | +++ | +++ | +++ | +++ |

| | Example 11 | Example 12 | Example 13 | Example 14 |
|---|---|---|---|---|
| Polymer of example 4 | 20 g | 20 g | 20 g | 20 g |
| Pigment paste comprising 40% by weight of pigment in isododecane | 5 g with DC Red 7 | 5 g with DC Red 7 | 5 g with black iron oxide | 5 g with black iron oxide |
| Disteardimonium hectorite (Bentone Gel ISD V from Elementis) | 10 g | 10 g | 10 g | 10 g |

| | | | | |
|---|---|---|---|---|
| Isododecane | 65 g | 45 g | 65 g | 45 g |
| 2-Octyldodecanol | — | 20 g | — | 20 g |
| Appearance of the film | Homogeneous film | Homogeneous film | Homogeneous film | Homogeneous film |
| Resistance to water | +++ | +++ | +++ | +++ |
| Non-tacky | +++ | +++ | +++ | +++ |
| Transfer-resistant | +++ | +++ | +++ | +++ |

The results obtained show that the polymers 1 and 4, with or without 2-octyldodecanol, form a non-tacky homogeneous film which does not transfer with the finger and which is resistant to water.

The invention claimed is:

1. A random or block copolymer resulting from the polymerization of:
   (a) 50% to 80% by weight, of the total weight of monomers, of isobornyl (meth)acrylate,
   (b) 5% to 30% by weight of maleic anhydride, and
   (c) 15% to 30% by weight of an additional (meth)acrylate monomer selected from the group consisting of $C_6$-$C_{16}$ alkyl (meth)acrylates.

2. The copolymer as claimed in claim 1, which results from the polymerization of:
   (a) 60% to 80% by weight, of the total weight of monomers, of isobornyl (meth)acrylate,
   (b) 5% to 25% by weight of maleic anhydride, and
   (c) 15% to 30% by weight of said additional (meth) acrylate monomer.

3. The copolymer as claimed in claim 1, which results from the polymerization of:
   (a) 50% to 80% by weight, of the total weight of monomers, of isobornyl (meth)acrylate,
   (b) 5% to 15% by weight of maleic anhydride, and
   (c) 15% to 30% by weight of said additional (meth) acrylate monomer.

4. The copolymer as claimed in claim 1, which results from the polymerization of:
   (a) 60% to 80% by weight, of the total weight of monomers, of isobornyl (meth)acrylate,
   (b) 5% to 12% by weight of maleic anhydride, and
   (c) 18% to 30% by weight of said additional (meth) acrylate monomer.

5. The copolymer as claimed in claim 1, which results from the polymerization of:
   (a) 50% to 80% by weight, of the total weight of monomers, of isobornyl (meth)acrylate,
   (b) 5% to 30% by weight of maleic anhydride, and
   (c) 15% to 30% by weight of $C_6$-$C_{16}$ alkyl acrylate monomer.

6. The copolymer as claimed in claim 1, which comprises isobornyl acrylate, 2-ethylhexyl acrylate and maleic anhydride.

7. The copolymer as claimed in claim 1, which has a weight-average molecular weight ranging from 5000 to 1 000 000 g/mol.

8. The copolymer as claimed in claim 1 being a random copolymer.

9. The copolymer as claimed in claim 3 being a random copolymer.

10. The copolymer as claimed in claim 5 being a random copolymer.

11. A composition comprising, in a physiologically acceptable medium, a polymer as claimed in claim 1.

12. The composition as claimed in claim 11, wherein the polymer is present in a content ranging from 0.1% to 10% by weight, with respect to the total weight of the composition.

13. The composition as claimed in claim 11, which comprises a hydrocarbon oil.

14. The composition as claimed in claim 11, which comprises an additive selected from the group consisting of water, fragrances, preservatives, fillers, colorants, UV-screening agents, oils, waxes, surfactants, moisturizing agents, vitamins, ceramides, antioxidants, agents for combating free radicals, polymers, thickeners, silicone oils and colorants.

15. The composition as claimed in claim 11, which a makeup composition comprising a volatile oil and a non-volatile oil.

16. The composition as claimed in claim 11, which is anhydrous.

17. The composition as claimed in claim 11, wherein the polymer is present in amount effective as a tightening agent for skin.

18. A cosmetic method for caring for or making up the skin or the lips, comprising the topical application to the skin or the lips of a composition as claimed in claim 11.

19. The method as claimed in claim 18, which is a cosmetic method for caring for the skin with the topical application to the skin of said composition.

20. The method as claimed in claim 19, which is intended to attenuate wrinkles.

* * * * *